United States Patent [19]

Hu et al.

[11] Patent Number: 4,561,449
[45] Date of Patent: Dec. 31, 1985

[54] AUDITORY-EVOKED-ACTION-POTENTIAL-MEASURING SYSTEM

[75] Inventors: Victor L. Hu, San Jose; Larry W. Mauldin, Mountain View; John J. Lee, Cupertino, all of Calif.

[73] Assignee: Minnesota Mining and Manufacturing Company, St. Paul, Minn.

[21] Appl. No.: 445,551

[22] Filed: Nov. 30, 1982

[51] Int. Cl.[4] .............................................. A61B 5/12
[52] U.S. Cl. ................................................... 128/746
[58] Field of Search ................... 128/746, 731–733, 128/734; 179/1 N

[56] References Cited

U.S. PATENT DOCUMENTS

| | | | |
|---|---|---|---|
| 3,392,241 | 7/1968 | Weiss et al. ...................... | 128/746 X |
| 3,799,146 | 3/1974 | John et al. ....................... | 128/746 X |
| 4,024,499 | 5/1977 | Bosscher ......................... | 128/746 X |
| 4,201,225 | 5/1980 | Bethea, III et al. ................. | 128/746 |
| 4,327,252 | 4/1982 | Tomatis .......................... | 128/746 X |
| 4,387,723 | 6/1983 | Atlee, III et al. ................... | 128/734 |
| 4,390,748 | 6/1983 | Zwicker .......................... | 128/746 X |

FOREIGN PATENT DOCUMENTS 2299004 10/1976 France ............................... 128/746

OTHER PUBLICATIONS

Mason et al.; "Simple Online Detector of Auditory Evoked Cortical Pot'ls; *Med. and Biol. Eng. and Comp.;* vol. 15, No. 6, 11-1977, pp. 641–647.

Lenhardt et al.; "Use of Computer Assisted Analysis of Auditory Nervous System Activ. in Pediatric Patients"; 3rd Ann. Symp. on Comp. Applic. in Med., 10-1979, pp. 669–671.

*Primary Examiner*—Lee S. Cohen
*Assistant Examiner*—Angela D. Sykes
*Attorney, Agent, or Firm*—Thomas E. Schatzel

[57] ABSTRACT

An auditory-evoked-action-potential-measuring system for measuring the hearing acuity of a subject, the system employing generators for permitting automatic system functionality testing and skin-electrode-contact impedance testing and a switching unit permitting the system to automatically select for measurement the larger of two auditory-evoked-action potentials.

11 Claims, 1 Drawing Figure

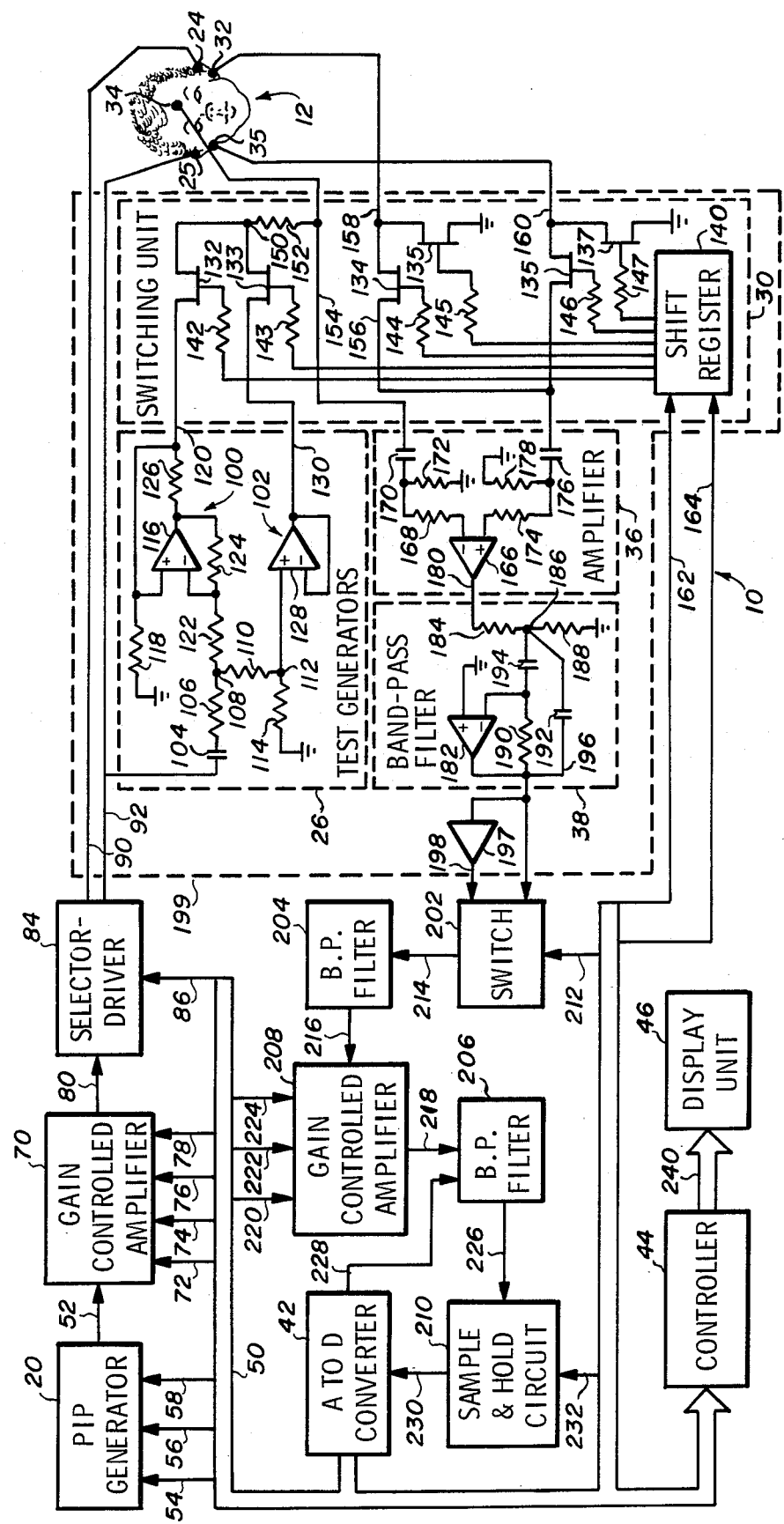

AUDITORY-EVOKED-ACTION-POTENTIAL-MEASURING SYSTEM

BACKGROUND OF THE INVENTION

1. Field of the Invention

The present invention relates to medical instruments generally and more particularly to an auditory-evoked-action potential-measuring system for use in measuring hearing acuity, the system having means for automatically testing the system and for selecting the larger of two auditory-evoked-action potentials.

2. Description of the Prior Art

It is generally accepted that the acquisition of basic vocabulary and language skills, including the acquisition of the basic units (words and speech sounds) and the rules for their combination (grammar and syntax), occurs during the period when a child is from six months to two and a half or three years of age. Obviously, the acquisition of such skills, and skills which depend thereon, may be significantly retarded if a child has a substantial undiagnosed hearing defect. Although spectacular diagnoses have been made by highly-skilled operators (audiologists) employing behavioral-type instruments such as continuous-tone audiometers to generate tones of selected frequency and level and observing the child's (subject's) response thereto, conventional hearing acuity measurements with such instruments rely upon a cooperating subject to report threshold levels. Obviously, such cooperation (tasks) are beyond the skill levels of children this young.

A prior-art-type system which does not require such cooperation directly measures the evoked-action potentials developed by a subject responsive to a stimulus. To facilitate the separation of the evoked-action potentials from other (EEG-type) brain-activity potentials, the above-mentioned prior-art-type evoked-action-potential measuring system employs a generator, called a pip generator, for periodically developing a signal from which a periodic acoustic stimulus may be developed. The generator periodically develops a tone-pip signal the frequency of the cycles of which occur at an auditory rate and the amplitude of the cycles of which is defined by an envelope having an attack portion and a decay portion both chosen to avoid "clicks." Additionally, the prior-art-type evoked-action-potential-measuring system employs circuitry for amplifying and filtering the evoked-action potentials and a cathode-ray-type unit for displaying the filtered potentials so that a trained and experienced operator may ascertain the evoked-action-potential levels (and possibly other parameters such as the latency thereof).

Evoked-action-potential-measuring systems are advantageous in that they permit the validation of auditory (and possibly other) systems of very young children, preferably as part of a standard well-baby check-up at 6 months of age. Unfortunately, the above-mentioned prior-art-type evoked-action-potential-measuring system is relatively complex and expensive and requires for its use the services of a trained and experienced operator.

Another problem is that evoked-action potentials are not always generated so as to appear symmetrical. In other words, it has been observed that with a significant number of subjects (perhaps 50%) the evoked-action potential measured at a lateral point (such as on the earlobe, on the mastoid or in the ear canal) on one side of the head with respect to a common point (such as the forehead) differs significantly in amplitude (perhaps by a factor of 2) from the amplitude of the potential measured on the other side. This lateralization is apparently independent of the side stimulated and does not appear to be related to dominance (as in right/left handedness). A low evoked-action-potential level may also be traced to an excessive skin-electrode-contact impedance.

SUMMARY OF THE PRESENT INVENTION

Therefore, objects of the present invention are to provide a relatively simple and inexpensive auditory-evoked-action-potential-measuring system which does not require the services of a trained and experienced operator.

Other objects of the present invention are to provide an auditory-evoked-action-potential-measuring system which automatically selects the larger of the evoked-action potentials developed on a left and a right electrode and tests for an excessive skin-electrode-contact impedance.

Briefly, the preferred embodiment of an auditory-evoked-action-potential-measuring system in accordance with the present invention employs a pip generator, a gain-controlled amplifier, a combined selector-driver and a pair of electro-acoustic transducers (earphones), the combination for generating a periodic acoustic stimulus. Additionally, the system employs a pair of generators including a voltage-source generator for system operation testing and a current-source generator for skin-electrode-contact-impedance testing, a switching unit, a left, a center and a right electrode and an amplifier. The switching unit is operative to selectively couple one of the test generators to the center electrode for testing and to couple various combinations of the electrodes to the amplifier both for testing and for coupling to the amplifier auditory-evoked-action potentials developed on the left or right electrode with respect to the center electrode. The electrodes are spaced apart from the transducers to prevent their being directly influenced thereby. Also employed are two additional gain-controlled amplifiers, three active band-pass (BP) filters, a sample-and-hold circuit and an analog-to-digital (A to D) converter for digitizing samples of the amplified and filtered auditory-evoked-action potentials. Finally, the system employs a controller and a display unit. In addition to coordinating the operation of the other elements of the system both for testing and for hearing acuity measuring, the controller stores the digitized samples, combines the samples with periodically corresponding samples and from the samples representing the larger of the auditory-evoked-action potentials developed on the left and the right electrode develops a signal for driving the display unit so as to indicate the corresponding hearing acuity.

Thus, the present invention is advantageous in that it provides a simple and inexpensive auditory-evoked-action-potential-measuring system for automatic testing and hearing acuity measuring all without the need of a trained and experienced operator.

These and other objects and advantages of the present invention will no doubt become apparent after having read the following detailed description of the preferred embodiment illustrated in the figure of the drawing.

IN THE DRAWING

FIG. 1 is a schematic diagram of the preferred embodiment of an auditory-evoked-action-potential-measuring system in accordance with the present invention.

DETAILED DESCRIPTION OF THE PREFERRED EMBODIMENT

In accordance with the present invention, illustrated in FIG. 1 of the drawing generally designated by the number 10 is the preferred embodiment of an auditory-evoked-action-potential-measuring system suitable for measuring the hearing acuity of, and, thus, for validating the hearing system of a subject represented by a child 12. As illustrated, system 10 employs as principal component a pip generator, designated 20, a pair of electro-acoustic transducers (earphones) including a left earphone 24 and a right earphone 25, a pair of generators, collectively designated 26, a switching unit 30, a left electrode 32, a center electrode 34, a right electrode 35, an amplifier 36, a band-pass (BP) filter 38, an analog-to-digital (A to D) converter 42, a controller 44 and a display unit 46.

Pip generator 20 is responsive to signals generated (in digital format) by controller 44 on a bus 50 and operative to generate (in analog format) tone-pip signals on a line 52. Specifically, at each of the times marked by a signal developed on a line 54 of bus 50, generator 20 generates a tone-pip signal the frequency of the cycles of which is controlled by the signals developed on a pair of lines of bus 50 which are designated 56 and 58. Preferably, the cycles of the tone-pip signals have a frequency of 500 hertz, 1000 hertz or 2000 hertz, respectively. The amplitude of each tone-pip signal is defined by an envelope having an attack portion and a decay portion both chosen to minimize system ringing to avoid "clicks."

Additionally, for testing, pip generator 20 generates (in analog format) a 40 hertz signal on line 52 at each of the times marked by the signal developed on line 54 when selected by the signals developed on lines 56 and 58. A suitable generator is disclosed in the U.S. Pat. application Ser. No. 428,312 entitled "A Tone-PiP-Signal Generator" filed on Sept. 29, 1982.

Also employed in system 10 is a gain-controlled amplifier 70 having a gain which is controlled by signals developed by controller 20 on four lines of bus 50, designated 72, 74, 76 and 78, to develop an amplified signal on a line 80 from a tone-pip signal (or test signal) developed on line 52. Specifically, amplifier 70 includes three operational amplifiers which are, preferably, portions of a device of the type that is commonly designated 353, and a pair of electronic switches each, preferably, of the type which forms a portion of a respective device of the type that is commonly designated CD4052BE. The first operational amplifier is connected in a (non-inverting) buffer configuration. In other words, the first operational amplifier, which has a non-inverting-input terminal, an inverting-input terminal and an output terminal, has the inverting-input and output terminals interconnected. The first electronic switch has three contacts which are analogous to the fixed contacts of a rotary-type switch and which are each coupled by a respective one of three voltage-divider resistors to the first operational-amplifier-output terminal, a fourth fixed contact which is (directly) connected to the output terminal, and, for selective connection to the other four contacts, a contact which is analogous to the movable contact of the rotary-type switch. This latter contact is coupled to circuit ground by another voltage-divider resistor and connected to the non-inverting-input terminal of the second operational amplifier which is also connected in the buffer configuration. Additionally, for contact selection, the first electronic switch has a pair of control terminals each of which is connected to a respective one of the two lines 72 and 74.

The output terminal of the second operational amplifier is coupled by a DC-blocking (AC-coupling) capacitor to a node which is coupled to circuit ground by the series combination of four voltage-divider resistors. The node and nodes at each of the junctures of the latter resistors are connected to respective fixed contacts of the second switch. The two control terminals of the second switch are connected to respective ones of the two lines 76 and 78; and, the movable contact of the switch is connected to the non-inverting-input terminal of the third operational amplifier. The inverting-input terminal of the third operational amplifier is coupled to circuit ground by a voltage-divider resistor and coupled by another voltage-divider (feedback) resistor to the amplifier output terminal which is (directly) connected to line 80.

A combined selector-driver 84 is employed for developing from the amplified signal developed on line 80 a signal suitable for driving a one of the electro-acoustic transducers (earphones) selected by a signal developed by controller 44 on a line 86 of bus 50. The transducer-driving signal is developed on a line 90 to drive the left transducer (designated 24) and developed on a line 92 to drive the right transducer (designated 25). More specifically, selector-driver 84 includes an electronic switch, preferably, of the type which forms a portion of a device that is commonly designated CD4053BE, and four operational amplifiers, which are, preferably, portions of a device of the type that is commonly designated TL74. The electronic switch, which functions in a fashion similar to a SPDT-type mechanical switch, has a contact, which is analogous to the movable contact in the SPDT-type switch and which is connected to line 80, a control terminal which is connected to line 86 and a pair of contacts which are analogous to the fixed contacts in the SPDT-type switch. Individually, each of the operational amplifiers is connected in the buffer configuration. In pairs, the operational amplifiers are connected in parallel, the non-inverting-input terminals of each pair of the operational amplifiers being connected together and the output terminals of each pair of the operational amplifiers being coupled together each by a respective one of a pair of balancing resistors. The non-inverting-input terminals of each pair of operational amplifiers is, additionally, connected to a respective one of the pair of fixed electronic-switch contacts; and, the node at the juncture at each pair of balancing resistors is connected to a respective one of the pair of lines 90 and 92.

The generators that are collectively designated 26 include a current-source generator which is generally designated 100 and which is employed for skin-electrode-contact-impedance testing and a voltage-source generator which is generally designated 102 and which is employed for testing and calibrating the system (10). A signal for driving the generators is developed from the right-transducer-driving signal developed on line 92 by a voltage divider formed by a DC-blocking capacitor 104, a voltage-divider resistor 106 connected in series with capacitor 104 between line 92 and a node 108, another voltage-divider resistor 110 connected between node 108 and a node 112, and a third voltage-divider resistor 114 connected between node 112 and circuit ground.

Current-source generator 100 is configured around an operational amplifier 116 having a non-inverting-input terminal coupled to circuit ground by a voltage-divider resistor 118 and connected to switching unit 30 by a line 120, an inverting-input terminal coupled to node 108 by a voltage-divider resistor 122, and an output terminal coupled to the inverting-input terminal by another voltage-divider (feedback) resistor 124 and coupled to line 120 by a voltage-divider (feedback) resistor 126. In the preferred embodiment, generator 100 develops a 2 microamp signal on line 120.

Voltage-source generator 102 is configured around another operational amplifier 128 which is connected in the buffer configuration. The non-inverting-input terminal of operational amplifier 128 is connected to node 112; and, the output terminal of the operational amplifier (which is connected to the inverting-input terminal thereof) is also connected to switching unit 30 by another line 130. In the preferred embodiment, generator 102 develops a 400 microvolt signal on line 130. Preferably, operational amplifiers 116 and 128 form portions of a device of the type which is commonly designated 353.

Switching unit 30 includes six field-effect transistors, which are designated 132–137, inclusive, for selectively coupling generator 100 or generator 102 to the left electrode (designated 32) for testing and for coupling various combinations of the electrodes to amplifier 36, and a shift register 140 for controlling the transistors. Specifically, for controlling the operative state of each of transistors 132–137, the gate of each transistor is coupled by a respective one of six current-limiting (device-protecting) resistors, designated 142–147, inclusive, to a respective output terminal of shift register 140. For selectively coupling generator 100 to left electrode 32, the source (or drain) of transistor 132 is connected to line 120; and, the drain (or source) of the transistor is connected to a node 150 which is coupled by a current-limiting (device-protecting) resistor 152 to a line 154 that is connected to the center electrode (designated 34). Transistor 133 is connected to selectively couple line 130, and, thus, generator 102, to node 150 and, thus, the left electrode (32). In other words, the source of the transistor is connected to line 130; and, the transistor drain is connected to node 150. Transistor 134 is connected to selectively couple a line 156, which forms one of a pair of differential input lines of amplifier 36, to a line 158, which is connected to the left electrode (designated 32); and, transistor 135 is connected to selectively couple line 158, and, thus, electrode 32, to circuit ground. Finally, a line 160, which is connected to the right electrode (designated 25) is selectively coupled to line 156 by transistor 136 and to circuit ground by transistor 137. The data-input terminal of shift register 140 is connected to a line 162 of bus 50; and, the shift-register clocking-input terminal is connected to another line, a line 164, of bus 50. In the preferred embodiment, transistors 132–137 are of the N-channel junction-type which is commonly designated 2N4393; and, preferably, shift register 140 forms a portion of a device of the type which is commonly designated 4015.

Although the left and right electrodes may each be located at any of a number of locations, such as, for example, on a respective earlobe, on a respective mastoid or in a respective ear canal, it has been found that each of the electrodes should be spaced apart from the electro-acoustic transducers (earphones) to prevent the transducers from inducing a potential on the electrode which may mask the respective auditory-evoked-action potential developed thereon. Suitable for use herein are the electrodes disclosed in U.S. Pat. applications Ser. Nos. 424,353, 424,387 and 424,425 all of which are entitled "Ear Canal Electrode" and all of which were filed on Sept. 27, 1982. Also suitable is the "Party Audiometer Accesory Support" disclosed in the U.S. patent application of common assignment by Damby et al.

In the preferred embodiment, amplifier 36 includes a device (designated 166) of the type which is commonly referred to as an instrumentation amplifier, which is commonly designated LM363 and which is suitable for providing a gain of approximately 100. Device 166 has an inverting-input terminal which is coupled by a current-limiting (device-protecting) resistor 168 to a node that is coupled to line 154 by a DC-blocking (AC-coupling) capacitor 170 and to circuit ground by a biasing resistor 172. Additionally, device 168 has a non-inverting-input terminal which is coupled by another current-limiting resistor 174 to a node that is coupled to line 156 by a DC-blocking capacitor 176 and to circuit ground by a biasing resistor 178. Device 166 also has an output terminal which is connected by a line 180 to band-pass filter 38.

Band-pass (BP) filter 38, that is of the active type, is configured around an operational amplifier 182 which is preferably of the type that forms a portion of a device commonly designated 353. In addition to operational amplifier 182, filter 38 includes a pair of voltage-divider resistors, one, designated 184, being connected between line 180 and a node 186 and the other, designated 188, being connected between node 186 and circuit ground. Further, filter 38 includes a pair of feedback elements, a resistor 190 connected between the output and inverting input terminals of operational amplifier 182 and a capacitor 192 connected between the output terminal of the operational amplifier and node 186. Finally, filter 38 includes, as a coupling element, a capacitor 194 connected between node 186 and the inverting-input terminal of operational amplifier 182. The output terminal of operational amplifier 182 is connected to a line 196; and, in this case, the non-inverting-input terminal of the operational amplifier is connected to circuit ground. In the preferred embodiment, filter 38 has a Q of approximately 1 and a center frequency of approximately 31.8 hertz.

Additionally, the system (10) employs an amplifier 197 for developing a signal on a line 198 by further amplifying the signal developed on line 196. An operational amplifier which, preferably, forms a portion of a device of the type that is commonly designated 353, is included in amplifier 197 with a resistor connected between the operational-amplifier-output terminal and the operational-amplifier-inverting-input terminal and another resistor connected from this latter terminal to circuit ground to cause the operational amplifier to provide a gain of approximately 101.

Preferably, those elements of system 10 which are collectively designated by the number 199 are packaged together and disposed in close proximity (a couple of feet) of the transducers and electrodes.

The system (10) also employs a switch 202, two more band-pass (BP) filters, designated 204 and 206, another gaincontrolled amplifier 208 and a sample-and-hold circuit 210. Switch 202 includes a switching device of the type which is commonly designated CD4053, the device being responsive to a signal developed by controller 44 on a line 212 of bus 50 and operative to couple the signal developed on the selected one of the two lines 196 and 198 to a line 214.

Band-pass (BP) filter 204, which is similar to filter 38, is operative to develop a further filtered signal on a line 216 from the signal developed on line 214.

Gain-controlled amplifier 208 includes a pair of operational amplifiers, preferably, of the type which form portions of a device of the type that is commonly designated 353, and a pair of electronic switches, preferably, one forming a portion of a device of the type commonly designated CD4052 and the other forming a portion of a device of the type commonly designated CD4053. The operational amplifiers are connected in cascade. In other words, line 216 is connected to the non-inverting-input terminal of the first operational amplifier; the output terminal of the first operational amplifier is connected to the inverting-input terminal of the second operational amplifier; and, the output terminal of the second operational amplifier is connected to a line 218. A respective one of two feedback resistors is connected between the output terminal and the inverting-input terminal of each of the operational amplifiers. Four gain-controlling resistors are each connected between a respective fixed contact of the first electronic switch and the inverting input terminal of the first operational amplifier. The movable contact of the first electronic switch is connected to circuit ground; and, the two control terminals of the electronic switch are connected to respective ones of two lines of bus 50, lines which are designated 220 and 222. Another gain-controlling resistor is connected between the inverting-input terminal of the second operational amplifier and one of the fixed contacts of the second electronic switch. The movable contact of the second electronic switch is also connected to circuit ground; and, the control terminal of the electronic switch is connected to another line of bus 50, a line which is designated 224.

Band-pass (BP) filter 206 develops a signal on a line 226 by further filtering the signal developed on line 218. Filter 206 differs from filter 38 in that the non-inverting-input terminal of the operational amplifier employed in filter 206 is connected to a line 228 to receive a reference potential developed thereon, rather than circuit ground.

Sample-and-hold circuit 210 develops a signal on a line 230 which represents the signal developed on line 226 frozen at times designated by a signal developed on a line 232. For this purpose, circuit 210 includes a charge-storing capacitor connected between a node and circuit ground, a pair of operational amplifiers, preferably of the type which form a portion of a device commonly designated TL74, and an electronic switch, preferably of the type which forms a portion of a device commonly designated CD4053. The operational amplifiers are each connected in the buffer configuration. One operational amplifier is connected to couple, buffered, the signal developed on line 226 to the electronic switch. The switch, which is controlled by a signal developed on line 232, is connected to selectively couple to the node and, thus, the capacitor, the signal buffered by the first operational amplifier. Finally, the second operational amplifier is connected between the node and line 230 to couple thereto a buffered representation of the signal stored by the capacitor.

Analog-to-digital (A-to-D) converter 42 includes a device, preferably, of the type commonly designated ADC0804, for, responsive to signals developed on bus 50, developing signals on bus 50 which represent, in digital format, the (analog) signal developed on line 230 and for developing the reference potential on line 228.

In addition to coordinating the operation of the other elements of the system (10), a controller 44 averages digitized signal samples with periodically cooresponding samples to separate from noise the periodic signals (signals representing auditory-evoked-action potentials and test signals) and measures the amplitude thereof. Preferably, controller 44 includes a microcomputing device of the type that is commonly designated 8031, a device of the type which is commonly designated 74LS373 for latching addressing signals developed by the microcomputing device, a pair of erasable-programmable-read-only-memory (EPROM) devices of the type which are commonly designated 2732 for storing instructions for execution by the microcomputing device, a number of devices of the type commonly designated LM339 for buffering and a pair of devices, one of the type commonly designated 8155 and the other of the type commonly designated 8156, for, with the buffering devices, interfacing the microcomputing device to both bus 50 and a bus 240, the latter for driving display unit 46.

Display unit 46 includes, in the preferred embodiment, three liquid-crystal-display (LCD) devices of the type commonly designated FE1OO1 each for displaying four 7-segment alphanumeric characters, three shift-register devices of the type commonly designated MD4332B for developing signals for driving two of the LCD devices from signals developed on bus 240 and two counter devices of the type commonly designated ICM7224 for developing signals for driving the other LCD device from signals developed on bus 240.

Operationally, before hearing acuity measurements are made, certain tests are performed. During the tests, signals are developed on bus 50 to select for generation by generator 20 the 40 hertz signal and to designate line 92 as the line on which the signal is to be developed to drive generator 26. To reduce the signal-averaging time required by controller 44 to separate signals employed during the test from noise, relatively large signals are employed. To compensate therefore, during the test, the signal developed on line 196 is selected rather than the further amplified signal developed on line 198. First, the functionality of the system (10) is tested. To this end, transistor 133 is turned on to couple to the inverting-input line (154) of amplifier 36 to the 40 hertz voltage-source signal developed by generator 102; transistors 134 and 135 are turned on to couple to circuit ground the non-inverting-input line (156) of the amplifier; and, the other transistors are turned off. The 40 hertz signal is amplified, filtered, sampled, digitized, averaged and the amplitude thereof is measured, much as auditory-evoked-action potentials are processed while hearing acuity measurements are being made. The result is stored for later use as a calibration standard.

Next, the skin-electrode-contact impedances are measured. First, transistors 132, 134 and 137 are turned on; and, the other transistors are turned off. As a result, the current developed by current-source generator 100 flows through transistor 132, the skin-electrode-contact impedance associated with the center electrode (34), the skin-electrode-contact impedance associated with the right electrode 35 and transistor 137 to circuit ground.

As the current flows through each impedance, a voltage drop is developed thereacross, the voltage drop being proportional to the magnitude of the respective impedance. Since transistor 134 is on, amplifier 36 is coupled (between center electrode 34 and left electrode 32) across the center electrode skin-electrode-contact impedance to permit the measurement of the magnitude thereof. (Since the current flow into amplifier 36 is negligible, a negligible voltage drop is developed across the left electrode skin-electrode-contact impedance to effect the measurements.)

Thereafter, transistor 134 is turned off and transistor 135 is turned on. The current path remains unchanged. However, amplifier 36 is coupled between the center electrode (34) and the right electrode 35 to permit the system to measure the voltage drop developed across the combination of center and right skin-electrode-contact impedances and, thus, the magnitude thereof. Having previously measured the magnitude of the center electrode skin-electrode-contact impedance, the right electrode skin-electrode-contact impedance is calculated by simple subtraction.

Finally, transistors 132, 134 and 135 are turned on; and, the other transistors are turned off. As a result, the current developed by current-source generator 100 flows through both the center and left electrode skin-electrode-contact impedances to develop thereacross a voltage drop which is measured to calculate the magnitude of the impedance combination. Again, the magnitude of the left electrode skin-electrode-contact impedance is calculated by simple subtraction.

Should the tests indicate that the system (10) is functioning properly and that the skin-electrode-contact impedances are not excessive, hearing acuity measurements are made. First, transistors 134 and 137 are turned on while the amplitude of the auditory-evoked-action potential developed on the left electrode (32) is measured (the other transistors having been turned off). Next, transistors 135 and 136 are turned on while the amplitude of the auditory-evoked-action potential developed on the right electrode 35 is measured. The level of the larger of the auditory-evoked-action potential is displayed on unit 46 as a measure of the subject's hearing acuity.

It is contemplated that after having read the preceeding disclosure, certain alterations and modifications of the present invention will no doubt become apparent to those skilled in the art. It is therefore intended that the following claims be interpreted to cover all such alterations and modifications as fall within the true spirit and scope of the invention.

What is claimed is:

1. A system for validating a subject's sensory system, the sensory system validating system comprising in combination:
   at least one transducer means for applying a stimulus to a subject:
   means for use with said transducer means for generating a stimulus at a periodic rate;
   first electrode means for detecting an evoked potential:
   means for use with said first electrode means for receiving a first evoked-action potential generated by said subject responsive to said periodic stimulus:
   second electrode means for detecting an evoked potential:
   means for use with said second electrode means for receiving a second evoked-action potential generated by said subject responsive to said periodic stimulus; and
   means for automatically identifying the larger one of said first and said second received evoked-action potential and for indicating the level thereof.

2. A system for validating a subject's sensory system, the sensory system validating system comprising in combination:
   means for generating a stimulus at a periodic rate and applying the stimulus to a subject
   first contact means for receiving a first evoked-action potential generated by the subject responsive to said periodic stimulus;
   second contact means for receiving a second evoked-action potential generated by said subject responsive to said periodic stimulus; and
   means for automatically identifying the larger one of said first and said second received evoked-action potentials and for indicating the level thereof, said identifying means including filter meanss for passing signals the frequency of which corresponds to said periodic rate; switching means for coupling a selected one of said first and said second received evoked-action potentials to said filter means; means for digitizing signals passed by said filter means; display means; and controller means for storing at least some of said digitized signals, for averaging one of said stored signals which correspond periodically, for so driving said switching means that averaged samples corresponding both said first and said second received evoked-action potentials are stored, for comparing the level represented by said stored signals to select those representing said larger one of said first and said second received evoked-action potentials, and for driving said display means so as to indicate the level of said larger one of said first and said second received evoked-action potentials.

3. A system for measuring the hearing acuity of a subject, the system comprising in combination:
   means for generating a tone-pip signal at a periodic rate;
   first electro-acoustic transducer means for generating an acoustic wave:
   first means for coupling at least some of said tone-pip signals to said first electro-acoustic transducer means whereby said acoustic wave is generated for periodically stimulating the subject;
   left electrode means for receiving a left auditory-evoked-action potential generated by said subject responsive to said periodic stimulus;
   right electrode means for receiving a right auditory-evoked-action potential generated by said subject responsive to said periodic stimulus;
   filter means for passing signals having a frequency corresponding to said periodic rate;
   second coupling means for coupling the auditory-evoked-action potential received on a selected one of said left and said right electrode means to said filter means; and
   identifying means for receiving the signals passed by said filter means, for driving said second coupling means to select in turn said left and said right electrode means, for identifying the larger one of said left and said right received auditory-evoked-action potentials, and for indicating the level thereof.

4. A system for measuring the hearing acuity of a subject as recited in claim 3 wherein said identifying means includes means for digitizing samples of said signals passed by said filter means; third means for coupling said signals passed by said filter means to said digitizing means; display means; and controller means for receiving and storing said digitized sample signals, for averaging ones of said stored digitized sample signals which correspond periodically, for so driving said second coupling means that averaged sample signals corresponding to both said left and said right received auditory-evoked-action potentials are stored and for driving said display means so as to indicate the level of said larger one of said left and said right received-auditory-evoked-action potentials.

5. A system for measuring the hearing acuity of a subject as recited in claim 4 wherein said third coupling means has means for sampling the level of said signals passed by said filter means and for storing the sample signals while said digitizing means is digitizing them.

6. A system for measuring the hearing acuity of a subject as recited in claim 4 further comprising second electro-acoustic transducer means and wherein said first coupling means is operative to couple each of said tone-pip signals to a selected one of said first and said second electro-acoustic transducer means.

7. A system for measuring the hearing acuity of a subject as recited in claim 4 further comprising means for generating a voltage-source signal having said periodic frequency and wherein said second coupling means is responsive to said controller means and operative to couple said voltage-source signal to said filter means for testing the operation of the system.

8. A system as recited in claim 4 wherein said left electrode means includes a center electrode and a left electrode for receiving said left auditory-evoked-action potential thereon with respect to said center electrode and wherein said right electrode means includes said center electrode and a right electrode for receiving said right auditory-evoked-action potential thereon with respect to said center electrode.

9. A system as recited in claim 8 further comprising means for generating a signal of constant mean current amplitude of said periodic rate and wherein said second coupling means is responsive to said controller means and operative to couple said constant-current signal to a one of said electrodes with respect to another one of said electrodes for obtaining an indication of the skin-electrode-contact impedance of at least one of said electrodes.

10. A system for measuring the hearing acuity of a subject as recited in claim 8 wherein said first electro-acoustic transducer means is sufficiently spaced apart from each of said electrodes so that signals induced by said electro-acoustic transducer means onto each of said electrodes is of a level which is less than a level sufficient to mask the one of said auditory-evoked-action potentials received thereon.

11. A system for validating a subject's sensory system, the sensory system validating system comprising in combination:

means for generating a stimulus at a periodic rate and applying the stimulus to a subject:

first contact means for receiving a first evoked-action potential generated by the subject responsive to said periodic stimulus;

second contact means for receiving a second evoked-action potential generated simultaneously with said first evoked-action potential by said subject responsive to said periodic stimulus; and means for automatically identifying the larger one of said first and said second received evoked-action potentials and for indicating the level thereof.

* * * * *

UNITED STATES PATENT AND TRADEMARK OFFICE
CERTIFICATE OF CORRECTION

PATENT NO. : 4,561,449

DATED : December 31, 1985

INVENTOR(S) : Victor L. Hu, Larry W. Mauldin and John J. Lee

It is certified that error appears in the above-identified patent and that said Letters Patent is hereby corrected as shown below:

Col. 6, line 12, "Damby" should read --Danby--.

Col. 10, line 20, "meanss" should read --means--.

Col. 10, line 30, insert "to" after "corresponding".

Signed and Sealed this

Thirty-first Day of March, 1987

Attest:

DONALD J. QUIGG

*Attesting Officer*   *Commissioner of Patents and Trademarks*